United States Patent [19]
Argiriadi et al.

[11] Patent Number: 5,468,502
[45] Date of Patent: Nov. 21, 1995

[54] IBUPROFEN ENHANCING SOLVENT SYSTEM

[75] Inventors: Andrew A. Argiriadi, Cherry Hill; Robert G. Blank, Hammonton, both of N.J.; David H. Giamalva, Glen Allen, Va.

[73] Assignee: American Home Products Corporation, Madison, N.J.

[21] Appl. No.: 359,489

[22] Filed: Dec. 20, 1994

[51] Int. Cl.⁶ ............................. A61K 9/64; A61K 31/19
[52] U.S. Cl. ............................................. 424/456; 514/570
[58] Field of Search ............................ 514/570; 424/456

[56] References Cited

U.S. PATENT DOCUMENTS

| | | | |
|---|---|---|---|
| 4,690,823 | 9/1987 | Lohner et al. | 424/456 |
| 5,071,643 | 12/1991 | Yu et al. | 514/570 |
| 5,134,127 | 7/1992 | Stilla et al. | 514/58 |
| 5,376,645 | 12/1994 | Stilla et al. | 514/58 |
| 5,376,688 | 12/1994 | Morton et al. | 514/786 |

OTHER PUBLICATIONS

R. G. Laughlin, "HLB from a thermodynamic Perspective,", J. Soc. Cosmet. Chem, 3rd, 371–392 (Nov. 1981).
"Encyclopedia of Emulsion Technology," vol. 1, pp. 348–355, Paul Becher, Editor, Marcel Dekker, Inc. New York and Basel (Nov. 1981).
G. D. Vaughan, "Using solubility parameters in cosmetics formulation," J. Soc. Cosmet. Chem. 36, 319–333, Sep./Oct. 1985.

*Primary Examiner*—Raymond Henley, III
*Assistant Examiner*—Keith Mac Millian
*Attorney, Agent, or Firm*—John W. Routh

[57] ABSTRACT

Solvent systems for enhancing the solubility of ibuprofen for encapsulation into soft gelatin capsules is provided by the addition of ammonium acetate to the solvent system.

10 Claims, No Drawings

5,468,502

IBUPROFEN ENHANCING SOLVENT SYSTEM

BRIEF DESCRIPTION OF THE INVENTION

The present invention is directed to solvent systems for enhancing the solubility of ibuprofen for encapsulation into soft gelatin capsules. More particularly the basic solvent systems are the well known non-ionic solvent systems for solubilizing ibuprofen and the solubility enhancing agent is ammonium acetate.

BACKGROUND OF THE INVENTION

The solvent systems for solubilizing pharmaceuticals such as ibuprofen for encapsulation into soft gelatin capsules are well known in the art. A typical system is described in U.S. Pat. No. 4,690,823 to Manfred Lohner et al which describes soft gelatin capsules containing a solution of from 15 to 30 parts by weight of ibuprofen in a polyoxyethylene-polyoxypropylene polymer or in a mixture of a polyalkylene glycol and a surfactant. Suitable surfactants exemplified are polyoxyethylene-(40)-glycerol trihydroxystearate polyoxy-ethylene-(20)-stearyl alcohol, and polyoxyethylene-(20)-sorbitan monostearate. Because of its detailed description of solvent systems for solubilizing ibuprofen, U.S. Pat. No. 4,690,823 is incorporated herein by reference in its entirety.

Another description of solvent systems for solubilizing pharmaceuticals such as ibuprofen for encapsulation is given in U.S. Pat. No. 5,071,643 to Man S. Yu et al which describes solvent systems for ibuprofen comprising polyethylene glycol containing 0.2 to 1.0 mole equivalents of an ionizing agent of the hydroxide species per mole equivalent of ibuprofen. Suitable ionizing agents disclosed are potassium hydroxide, sodium hydroxide and ammonium hydroxide. The disclosure of U.S. Pat. No. 5,071,643 is also incorporated herein in its entirety.

U.S. Pat. No. 4,690,823 exemplifies solutions for incorporating into soft gelatin capsules of a suitable size wherein 0.880 grams of solution contains 200 milligrams or about 23% ibuprofen. U.S. Pat. No. 5,071,643 discloses solutions containing as high as 67% ibuprofen. The ionizing agents used as solubilizing enhancers for ibuprofen contain a highly reactive hydroxide ion which may react with other ingredients in the solution or with the capsule shell.

BRIEF SUMMARY OF THE INVENTION

According to this invention, the solubility of ibuprofen in conventional solvent systems is enhanced by up to 55% by incorporating into such systems ammonium acetate in an amount of about 1%–10% by weight, preferably about 5%–10% by weight, based on the weight of the clear solution. The resulting system is a clear microcolloidal solution of ibuprofen maintained stable by the buffering effect of the ammonium acetate.

The conventional solvent systems to be enhanced are those of the prior art such as polyethoxylated surface active agents having a hydrophile-lipophile balance within the range of 8 to 25 and polyalkylene glycol polymers having a hydrophile-lipophile balance within the range of 8 to 25 either alone or together with a solvent system having a solubility parameter within the range of between 8.0 and 15.0.

DETAILED DESCRIPTION OF THE INVENTION

The present invention is directed to a pharmaceutically acceptable highly concentrated clear microcolloidal solution of ibuprofen suitable for filling soft gelatin capsules for oral administration. The clear microcolloidal solutions contain at least 25% by weight of ibuprofen, preferably at least 33% by weight of ibuprofen. The ibuprofen is dissolved in an admixture comprising 1% to 10% by weight of water and 90% to 99% by weight of at least one of two pharmaceutically acceptable non-ionic materials which are (a) polyethoxylated surface active agents having a hydrophile-lipophile balance within the range of 8 to 25, (b) polyalkylene glycol polymers having a hydrophile-lipophile balance of 8 to 25, either alone or in admixture with a solvent system having a solubility parameter between 8.0 and 15.0.

Accordingly, the pharmaceutically acceptable highly concentrated clear microcolloidal solutions of the invention contain, based on the weight of the solution, at least about 25% by weight of ibuprofen, about 1% to 10% by weight of water, and about 50%–74% by weight of at least one of either a non-ionic polyethoxylated surface active agent or a non-ionic polyalkylene glycol alone or in combination with the solvent system having a solubility parameter within the range 8.0 and 15.0, and about 1%–10% by weight of ammonium acetate as the solubility enhancer.

Preferably, the non-ionic polyethoxylated surface active agent is a polyoxyethylene sorbitan derivative such as a fatty acid ester having a molecular weight of about 1100–1300 and the non-ionic polyalkylene glycol polymer is a polyethylene glycol polymer having a molecular weight of about 200–600. The solvent system having a solubility parameter of 8.0–15.0 preferably is polyethylene glycol. Most preferably, it is polyethylene glycol 400.

The hydrophile-lipophile balance is known in the literature and to the art as the HLB. See, for example, "HLB, from a thermodynamic perspective" by R. G. Laughlin in J. Soc. Cosmet, Chem., 32, 371–392 (November 1981), and "Encyclopedia of Emulsion Technology" Volume 1, pages 348–355, Edited by Paul Becher, Marcel Dekker, Inc. New York and Basel.

THE POLYETHOXYLATED SURFACE ACTIVE AGENTS

There are readily available listings of non-ionic polyethoxylated surface active agents having HLB numbers within the range 8–25 such as in the Encyclopedia of Emulsion Technology cited above at pages 355–359. These polyethoxylated surface active agents must be pharmaceutically acceptable and the agent or mixture of agents must have an HLB within the range of 8–25. For example, 50% of an agent having an HLB of 10 mixed with 50% of an agent having an HLB of 20 would produce an acceptable agent mixture having an HLB of 15.

Typical of these non-ionic polyethoxylated surface active agents are the polyoxyethylene ethers of various alcohols and fatty acids such as the polyoxyethylene sorbitan fatty acid esters, i.e., Polysorbates 20, 40, 60 and 80, which are available in NF grades and have molecular weights of about 1100–1300. Also suitable with their corresponding HLB numbers are the following. In the listing, POE stands for polyoxyethyl and the following numeral is the number of ethylene oxide units in the molecule.

TABLE 1

| Chemical designation | HLB number |
| --- | --- |
| POE (5) sorbitan monooleate | 10.0 |
| POE (20) sorbitan tristearate | 10.5 |
| POE (20) glycerol monostearate | 13.1 |
| POE (4) sorbitan monolaurate | 13.3 |
| POE (24) cholesterol | 14.0 |
| POE (20) sorbitan monostearate | 14.9 |
| POE (20) sorbitan monooleate | 15.0 |
| POE (20) sorbitan monopalmitate | 15.6 |
| POE (20) sorbitan monolaurate | 16.9 |
| POE (25) soyasterol | 17.0 |
| POE (20) castor oil (ether, ester) | 18.1 |

THE POLYALKYLENE GLYCOL POLYMERS

Polyalkylene glycol polymers such as polyethylene glycol polymers and polypropylene glycol polymers are also known as polyoxyalkylene glycol polymers and are marketed respectively as "CARBOWAX®" by Union Carbide Chemicals and Plastics Company Inc. of Danbury, Conn. and by Dow Chemical Company of Midland, Mich. under the "E" series designation. The polyoxyalkylene glycol polymers are marketed in NF grades and are designated PEG for polyethylene glycol and PPG for polypropylene glycol. The numeral following the designation stands for the number of alkylene oxide units in the molecule. In another nomenclature, the number which follows the designation indicates the average molecular weight of the compound. Liquid PEGs (Grades 200–600) are clear, colorless or slightly yellowish, viscous liquids. Solid PEGs are white or off-white in color and range in consistency between pastes and waxy flakes. All grades are soluble in water and miscible in all proportions with other PEGs, after melting if necessary. Acceptable PEGs having an HLB range of 8–25 are PEG-4, PEG-6, PEG-8, PEG-12 and PEG-20 having average molecular weights of 200–1000, preferably 200–600, alone or, if necessary, in combination.

Block copolymers of polyoxyethylene and polyoxypropylene segments are included in the family of polyoxyalkylene glycol polymers and are marketed under the designation PLURONICS® by the BASF Corporation of Parsippany, N.J. The HLB numbers for these polyoxyalkylene polymers and copolymers are given in the manufacturer's brochures. For example, the brochure for the PLURONICS® indicates those with an HLB number of 10–18 function as solubilizers.

Pharmaceutically acceptable solvent systems having solubility parameters within the range 8.0 and 15.0 are also well known in the art. Typical solvent systems together with their solubility parameters are given in an article by C. D. Vaughan entitled "Using solubility parameters in cosmetics formulation" appearing in J. Soc. Cosmet. Chem., 36, 319–333 (September/October 1985) at pages 329–331. Single solvents or any combination of solvents that will provide a solubility parameter range of 8.0–15.0 are acceptable. A mixture of water and propylene glycol is typical and is the preferred solvent system.

Other suitable solvent systems having solubility parameters within the range 6.0 and 23.4 include the following.

TABLE 2

| Chemical designation | Solubility Parameter ($\Delta$) |
| --- | --- |
| Squalane | 6.03 |
| White Mineral Oil | 7.09 |
| Olive Oil | 7.87 |
| Glyceryl Stearate (mono) | 8.31 |
| Sorbitan Laurate | 8.61 |
| Capric Acid | 8.88 |
| Castor Oil | 8.90 |
| Cetyl Alcohol | 8.94 |
| Glyceryl Laurate | 9.08 |
| Caprilic Acid | 9.35 |
| Cholesterol | 9.55 |
| Polypropylene Glycol - 4 | 9.89 |
| Triacetin | 10.77 |
| Polyethylene Glycol - 8 | 11.34 |
| Sorbic Acid | 11.97 |
| Alcohol, Ethyl | 12.55 |
| Propylene Glycol | 14.00 |
| Glycerin | 16.26 |
| Water | 23.40 |

The preferred solvent systems having solubility parameter within the range 8.0 and 15.0 are alcohols, polyols, acids and fatty acid esters each having 2–21 carbon atoms.

The invention will now be described in more detail by means of the specific examples.

EXAMPLE 1

This example sets forth the procedure for the preparation of a solvent system of the invention for enhancing the solubility of ibuprofen for encapsulation into soft gelatin capsules.

The following constituents were mixed with stirring in a flask while heating to 55°–65° C. on a steam bath with hot water.

| | |
| --- | --- |
| Polyethylene Glycol 400, NF | 5.000 grams |
| Polysorbate 80, NF | 1.009 grams |
| Propylene Glycol, NF | 1.004 grams |
| Purified Water | 0.5 milliliters |

Polyethylene Glycol 400, NF has an average number of oxyethylene groups of 8–10 and an average molecular weight of 380–420.

Polysorbate 80 is sorbitan mono-9-octadecanoate having a molecular weight of 1309.

The admixture was permitted to cool to 55° C. and to the admixture were added successively with stirring 0.530 gram of ammonium acetate and then 5.007 grams of ibuprofen. Some ammonium acetate crystals remained in the bottom of the flask at 55° C. but appeared to be dissolved on standing overnight. The solution was clear and analysis indicated an ibuprofen content of 38.4% by weight based on the weight of the solution.

EXAMPLE 2

Following the procedure of Example 1, another solvent system of the invention was prepared having the components as set forth below.

| | |
| --- | --- |
| Polyethylene Glycol 400, NF | 39.375 pbw |

-continued

| | |
|---|---|
| Propylene Glycol, NF | 7.875 pbw |
| Polysorbate 80, NF | 7.875 pbw |
| Ammonium Acetate (1/1 with Water) | 7.875 pbw |
| | 63.000 pbw |

This solvent system dissolved 37 pbw of ibuprofen and the final solution was clear. The clear microcolloidal solution containing 37% by weight of ibuprofen was encapsulated in a gelatin capsule in an amount providing 200 milligrams of ibuprofen. The resulting gelcap was clear.

EXAMPLE A

In contrast to the above, a solvent solution without ammonium acetate was made up as follows:

| | |
|---|---|
| Polyethylene Glycol 400, NF | 47.5 pbw |
| Propylene Glycol, NF | 9.5 pbw |
| Polysorbate 80, NF | 9.5 pbw |
| Purified Water | 9.5 pbw |
| | 76 pbw |

This solvent system dissolved only 24 pbw of ibuprofen.

One of the advantages of using the relatively neutral salt, ammonium acetate, as the solubility enhancing agent for ibuprofen, is that the chemistry of the ibuprofen in the microcolloidal solution is not changed. Also, the relatively neutral buffered solution is more compatible with the soft gel capsule.

We claim:

1. In a pharmaceutically acceptable highly concentrated clear microcolloidal solution of ibuprofen suitable for filling soft gels for oral administration comprising, based on the weight of the clear solution, at least about 25% by weight of ibuprofen, about 1%–10% by weight of water and about 50%– 74% of at least one pharmaceutically acceptable solubilizing material selected from the class consisting of non-ionic polyethoxylated surface active agents having a hydrophile-lipophile balance within the range of 8 to 25 and non-ionic polyalkylene glycol polymers having a hydrophile-lipophile balance within the range of 8 to 25 alone or in combination with a solvent system having a solubility parameter within the range 8.0 and 15.0, the improvement which comprises incorporating into the solution as an ibuprofen solubility enhancer about 1% to 10% by weight of ammonium acetate.

2. The pharmaceutically acceptable highly concentrated clear microcolloidal solution of claim 1 wherein one pharmaceutically acceptable solubilizing material is a non-ionic polyethoxylated surface active agent.

3. The pharmaceutically acceptable highly concentrated clear microcolloidal solution of claim 2 wherein the non-ionic polyethoxylated surface active agent is a polyoxyethylated sorbitan derivative having a molecular weight of about 1100– 1300.

4. The pharmaceutically acceptable highly concentrated clear microcolloidal solution of claim 1 wherein one pharmaceutically acceptable solubilizing material is a non-ionic polyalkylene glycol polymer.

5. The pharmaceutically acceptable highly concentrated clear microcolloidal solution of claim 4 wherein the polyalkylene glycol polymer is a normally liquid polyethylene glycol having a molecular weight of about 200–600.

6. The pharmaceutically acceptable highly concentrated clear microcolloidal solution of claim 1 wherein the solvent system having a solubility parameter within the range of 8.0 to 15.0 is selected from the class consisting of alcohols, polyols, acids and fatty acid esters each having 2–21 carbon atoms.

7. The pharmaceutically acceptable highly concentrated clear microcolloidal solution of claim 6 wherein the solvent system is propylene glycol.

8. The pharmaceutically acceptable highly concentrated clear microcolloidal solution of claim 1 wherein the pharmaceutically acceptable solubilizing materials are a non-ionic polyethoxylated surface active agent and a non-ionic polyalkylene glycol polymer.

9. The pharmaceutically acceptable highly concentrated clear microcolloidal solution of claim 8 wherein the polyethoxylated surface active agent is a polyoxyethylated sorbitan derivative, wherein the polyalkylene glycol polymer is a normally liquid polyethylene glycol having a molecular weight of about 200–600 and wherein the solvent system having a solubility parameter within the range of 8.0 to 15.0 is selected from the class consisting of alcohols, polyols, acids and fatty acid esters each having 2–21 carbon atoms.

10. The pharmaceutically acceptable highly concentrated clear microcolloidal solution of claim 9 wherein the polyethoxylated surface active agent is polyoxyethylene 20 sorbitan monooleate and the polyalylene glycol polymer is polyethylene glycol having an average molecular weight at 380–420 in combination with propylene glycol.

* * * * *